United States Patent [19]

Hrebeniuk

[11] Plant 4,221

[45] Mar. 7, 1978

[54] POINSETTIA PLANT

[75] Inventor: Alexander Hrebeniuk, Perkasie, Pa.

[73] Assignee: Mikkelsens, Inc., Ashtabula, Ohio

[21] Appl. No.: 780,985

[22] Filed: Mar. 24, 1977

[51] Int. Cl.[2] ..... A01H 5/00

[52] U.S. Cl. ..... Plt./86

[58] Field of Search ..... Plt./86

*Primary Examiner*—Robert E. Bagwill

*Attorney, Agent, or Firm*—Donald D. Jeffery

[57] ABSTRACT

A poinsettia cultivar which appears to be a tetraploid due to its heavy thick leaves, stiff thick stems and the appearance of the cyathias. The bract color is deep, bright red, and the cultivar is also characterized by fast rooting, excellent cutting production, self branching habit, and long lasting bracts and foliage.

1 Drawing Figure

1

The present invention relates to a new and distinctive red cultivar of poinsettia plant known by my identification number 75-HF-1, and botanically known as *Euphorbia pulcherrima.*

The new cultivar is the result of a controlled cross using the cultivar Wonder Star disclosed in my U.S. Plant Pat. No. 3,917 as the seed parent and a seedling of the cultivar Eckespoint C-1 as the pollen parent. The new cultivar has been asexually reproduced by cuttings in my greenhouses at Perkasie, Pa., and has been found to retain its distinctive characteristics through successive propagations.

The following characteristics distinguish the new cultivar from its parent and from other poinsettias commercially known and used in the floriculture industry:

1. The general appearance of the true flowers (cyathias) would indicate my new cultivar is a tetraploid.

2. The heavy thick leaves and stiff thick stems further confirms that this new cultivar is a tetraploid.

3. On the premise that the new cultivar is a tetraploid, the most significant characteristic of the new cultivar is the habit of self branching from the base of the stem without removal of the terminal tip; apparently this characteristic has not been observed before in tetraploid poinsettias. Also it is self branching on soft vegetative growth in the winter months.

4. Although there is some resemblance to my cultivar Wonder Star, the following are distinct differences: the foliage of my new cultivar is slightly larger than Wonder Star, the bracts are a deeper, brighter and clearer shade of red, and the cyathias remain longer under adverse light and temperature conditions than Wonder Star.

5. With the characteristic of spontaneous self branching, the production of cuttings is greater than in Wonder Star, a most important factor for the commercial propagator. The rooting time for cuttings of my new cultivar is 25 to 30% faster in the summer and up to 50% faster in the winter, a most significant difference from Wonder Star.

6. The total bract head is larger than that of Wonder Star because the bracts are larger and there are more of them so that there is very little open space around the center. Also the bracts tend to remain flat for a longer period of time. The cyathias are quite distinct and greater in number than in Wonder Star. The bracts and foliage are extremely long lasting, holding up in my home in dark areas better than any other poinsettias tested to date.

2

The accompanying colored photographic drawing illustrates the overall appearance of the new cultivar, with the colors being as true as possible to obtain in color reproductions of this type. The photograph clearly shows self branching in the lower areas of an unpinched plant.

The following is a detailed description of the new cultivar based on plants produced under commercial practices in my greenhouses at Perkasie, Pa. Color references are to the Royal Horticultural Society Colour Chart except where general color terms are referred to.

Parentage: Wonder Star crossed with a seedling of Eckespoint C-1.

Form of plant: Compact, upright. May be grown either with or without removal of the terminal tip; when pinched the laterals fill out more thereby giving a fuller plant.

Growth habit: Slow, with vigorous stems, and spontaneous self branching in all seasons.

Rooting: Short vegetative cuttings about 2–2½" long will root in 15–20 days in the summer in small pots and in 25–30 days in the winter months at 68°–70° F. Roots are thick indicating tetraploid.

Blooming habit: Flowering response occurs under natural short days beginning in late September/early October and full bloom is in early December. The cyathias continue to develop into February. The bracts remain intact until late spring. On self branching shoots, the bracts and cyathias may not develop properly if they are over crowded by the foliage or by closeness of adjoining plants.

Blooming season: Natural flowering occurs by early December if night temperatures are 60°–62° F. Being a short day plant, flowers can be induced in any season by using light and blacking out materials as commonly practiced by commercial growers.

Foliage:

*Size.*—2½" to 3" wide by 3" to 4" long under my growing conditions. Leaf petiole from 3" on lower foliage to 1" on upper foliage.

*Quantity.*—Near average for the normal rate of growth. The amount and size of foliage is quite variable according to the existing conditions of the total plant environment.

*Color.*—New Foliage — upper side — approximately 137A; under side — 137C-D. Old Foliage — upper side — dark green near 139A;under side — near 137B-C.

*Shape.*—Ovate to oval.

*Texture.*—Upper side — glabrous; under side — veins strongly protruding; veination — pinnate.

*Edge or margin.*—In strongly vegetative plants some leaves are lobed, in reproductive plants margin becomes entire.

*Aspect.*—The petioles are nearly horizontal, but the older lower foliage will tend to pull downward.

*Disease resistance.*—No foliage or bract diseases seen to date. Roots do not appear to have any particular resistance to common root rots.

Flowers (cyathia):

*Borne.*—Each on heavy strong pedicels attached to heavy stems originating from the apex. There is a tendency for flowering stems to continue growth into January/February.

*Quantity.*—In the original exposure of cyathias, up to 12–15, but additional cyathias develop as older ones drop off.

*Continuity.*—Development of cyathias has been observed for as long as 3 months.

*Bracts.*—The primary bracts below the cyathias have the shape and size of the leaves. The secondary bracts developing with cythias tend to be narrow and long, measuring 1″–1½″ wide by 2½″–3″ long. Red color holds extremely well in home environment at 65° F. Color: top — red 45B; under — red 46C.

*Reproductive organs.*—Stamens: Color, dark red 46A. Pollen: Color, yellow 21B. Styles: Color, red 46A. Ovaries: Color, yellow green, when maturing 146A.

I claim:

1. A new and distinct cultivar of poinsettia plant particularly characterized as to novelty by the combined characteristics of heavy thick leaves, stiff thick stems and appearance of cyathias all of which tend to indicate that the cultivar is a tetraploid; self branching from the base of the stem without removal of terminal tips; deep, bright red bract color; fast rooting in both summer and winter and excellent cutting production; long lasting bracts and foliage, and relatively large total bract head.

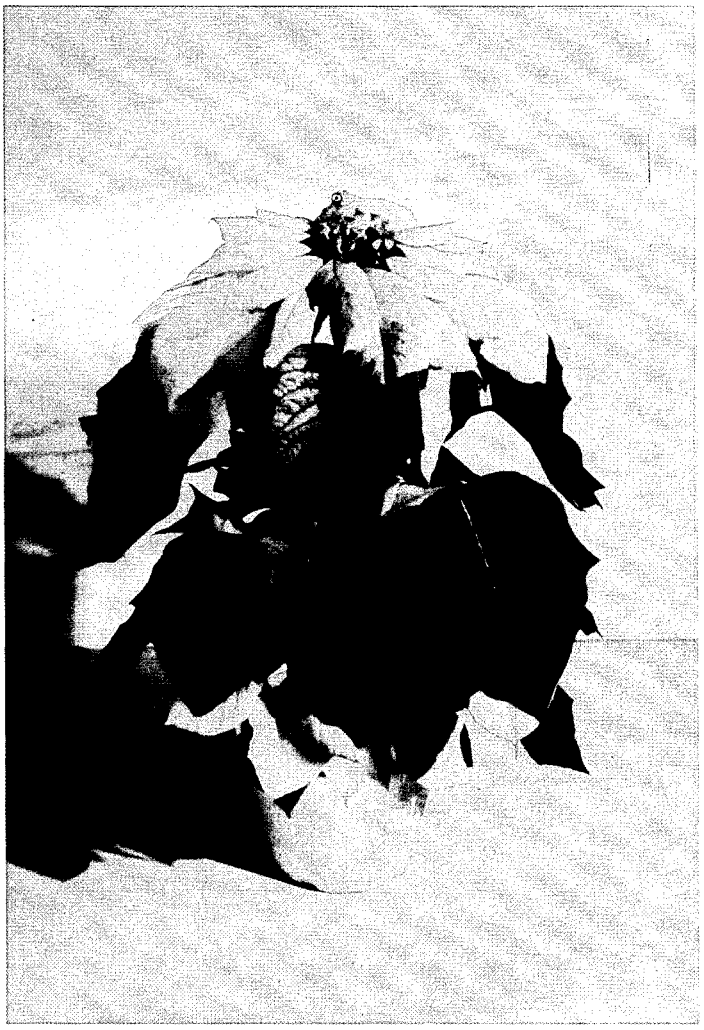

* * * * *